United States Patent [19]

Zacharias et al.

[11] Patent Number: 4,969,362

[45] Date of Patent: Nov. 13, 1990

[54] DUAL ELEMENT TRANSDUCER

[75] Inventors: Ellis M. Zacharias, Broken Arrow; Lawrence T. Riley; Henry E. Ryer, both of Tulsa, all of Okla.

[73] Assignee: Nusonics, Inc., Tulsa, Okla.

[21] Appl. No.: 367,932

[22] Filed: Jun. 19, 1989

[51] Int. Cl.$^5$ ............................................. G01N 9/24
[52] U.S. Cl. ...................................... 73/597; 73/61 R
[58] Field of Search .................... 73/597, 32 A, 61 R, 73/861.27, 861.28; 310/335

[56] References Cited

U.S. PATENT DOCUMENTS

| | | | |
|---|---|---|---|
| 3,715,709 | 2/1973 | Zacharias Jr. et al. | 73/861.27 |
| 3,890,423 | 6/1975 | Zacharias Jr. | 310/335 |
| 4,850,220 | 7/1989 | Asano et al. | 73/861.28 |

FOREIGN PATENT DOCUMENTS 1114942  9/1984  U.S.S.R. ............................. 73/597

Primary Examiner—Hezron E. Williams
Assistant Examiner—Louis M. Arana
Attorney, Agent, or Firm—Head and Johnson

[57] ABSTRACT

A transducer for use in measuring the sound velocity characteristics of a fluid medium formed of a transducer body having an access end and an opposed active end, the body having spaced apart first and second cylindrical openings therein extending from the access to the active end, a first and second acoustic window member sealably closing each of the cylindrical openings in the body at the active end, first and second transducer crystal elements within, respectively, the first and second openings and in sonic contact with the respective window acoustic members, a sound reflector affixed to the transducer body at the active end providing a first target surface coincident with the cylindrical axis of the first opening and providing a second target surface coincident with the cylindrical axis of the second openings, the target surfaces being spaced from the body active end and each being in a plane inclined toward the other defining a sonic path from the first acoustic window member to the first target surface, from the first target surface to the second target surface and from the second target surface to the second acoustic window member and a longitudinal slot formed in the body between the cylindrical openings providing acoustic isolation between the crystal elemens.

6 Claims, 2 Drawing Sheets

DUAL ELEMENT TRANSDUCER

SUMMARY OF THE INVENTION

Transducers that are used in apparatus for measuring the velocity of sound in liquids employ one or two piezoelectric elements. In those employing one piezoelectric element, this element serves as both transmitter and receiver on a time-shared basis. U.S. Pat. No. 4,763,513 illustrates a single element transducer which functions in conjunction with a reflector that is spaced from the element (item 188 in FIG. 3 of U.S. Pat. No. 4,763,513).

An advantage of the single element design over those employing two elements is that it is more compact and simpler in construction, hence less costly to manufacture. It usually performs well in the measurement of sound velocity in liquids when the ultrasonic absorption and scattering losses in the liquid are low as they usually are in many liquids, such as water, refined hydrocarbons and may types of acids, bases and other solutions of aqueous and non-aqueous compositions. However, the single element design may not perform well in lossy liquids such as those that exhibit high ultrasonic absorption or scattering. High concentrations of sodium hydroxide, sugar, acetic acid, formic acid and various synthetic rubber suspensions in water are examples of lossy liquids where a single element transducer may not perform well.

When used in a lossy liquid the single element transducer may have insufficient acoustic sensitivity due to self-generated noise that occurs after the transducer is energized. Typically, the transducer is energized by the application of a single, short duration, voltage pulse. When properly dampened, the element will vibrate briefly in its thickness mode, thereby creating a compression wave in the liquid. The wave propagates through the liquid to the reflector where it is reflected back to the element. The time between excitation of the element and arrival of the reflected wave indicates the sound velocity in the liquid.

A problem arises when the liquid is lossy because the amplitude of the reflected wave may be too small to be detected in the presence of the transducer self noise which occurs after the transducer is excited. This self noise is at a maximum immediately following excitation and diminishes exponentially with time. If it does not diminish fast enough, there may be sufficient self noise present to mask the reflected wave when it arrives. This problem is inherent in a single element design and even when adequate damping is applied to the element, reverberation noise within the transducer body may persist long enough to mask the reflected wave.

A solution to the problem is found in the two element transducer in which one element serves as the transmitter and the other as the receiver. The exponentially decaying self noise of the transmitter is of little concern provided there is sufficient acoustic isolation between transmitting and receiving elements.

One version of the two element transducer is illustrated in FIG. 8 of U.S. Pat. No. 3,890,423. Another is shown in FIG. 1 of BREWERS DIGEST article "The Determination of Yeast Slurry Consistency and Wort Plato" by M. F. Feil and Ellis M. Zacharias, Jr., Volume 46, Number 11, Page 76. Both of these two element designs employ cylindrical bodies which offer only a limited amount of acoustic isolation between the two elements. While both designs result in a reduction in self noise and better capability for detecting the reflected wave than does the single element design, there is need for further reduction in self noise.

In both of the two element designs the self noise results from acoustic coupling from the transmitting element to the receiving element through the transducer body. The close spacing of elements and sharing of a common acoustic window in the design of FIG. 8 in U.S. Pat. No. 3,890,423 accounts for a rather high degree of acoustic coupling between the two elements. While the two elements are spaced farther apart in the design of FIG. 1 of the BREWERS DIGEST article, there is nonetheless, a direct path for self acoustic noise from transmitting element to receiving element through the ring-shaped body of the transducer.

This invention is an improved dual element (two element) transducer. In one embodiment of the invention, the body is flat rather than cylindrical in shape and employs a slot through the body to acoustically isolate the two elements. Evaluation of an experimental model verified that the amount of acoustic coupling between the elements is greatly reduced.

Another improvement offered by this invention is reduced manufacturing costs since the entire transducer is fabricated from one-half inch flat stock (for two megahertz elements—thicker stock would be required for elements operating at a lower acoustic frequency). Moreover, the reduction in thickness compared with predecessor designs makes the new design better suited to small spaces.

Another improvement in the design is the tilting of the reflector about one degree out of the normal reflector plane to reduce the influence of reflections between elements. In earlier designs, such as those above referenced, the acoustic wave emitted from the transmitting element would travel through the liquid to the receiving element, then be reflected back to the transmitter, back to the receiver, and continue back and forth until the reflection was ultimately dissipated. These multiple reflections are undesirable because the may appear as a precursor to the desired reflected wave and cause an error in the measurement of wave travel time (and thus sound velocity). The resultant error can be substantial in low loss liquids such as water and in some instances may impair transducer operation.

It has been found that a reflector tilt of approximately one degree diminishes the reflection problem when the length of the acoustic path through the liquid is in the order of three inches. A greater tilt will be necessary for shorter paths and lesser tilt for longer paths.

In practicing the invention it is preferable that both transducer elements employ damping means similar to that described in the various figures of U.S. Pat. No. 4,763,513, as well as those taught in earlier U.S. Pat. No. 3,890,423. The transducer body may be fabricated from a variety of metals and may also be fabricated from a selection of acoustically transparent plastic material such as PVC (polyvinyl chloride), CPVC (chlorinated polyvinyl chloride) and PVDF (polyvinylidene fluoride) where chemical aggressiveness of the liquid so indicates.

For more details as to the invention, reference may be had to the following description of the preferred embodiment and claims taken in conjunction with the attached drawings.

Description of the Drawings

FIG. 1 is shown partially cut away to reveal details of the arrangement of one of the transducers.

Description of the Preferred Embodiment

Figures 1, 2:
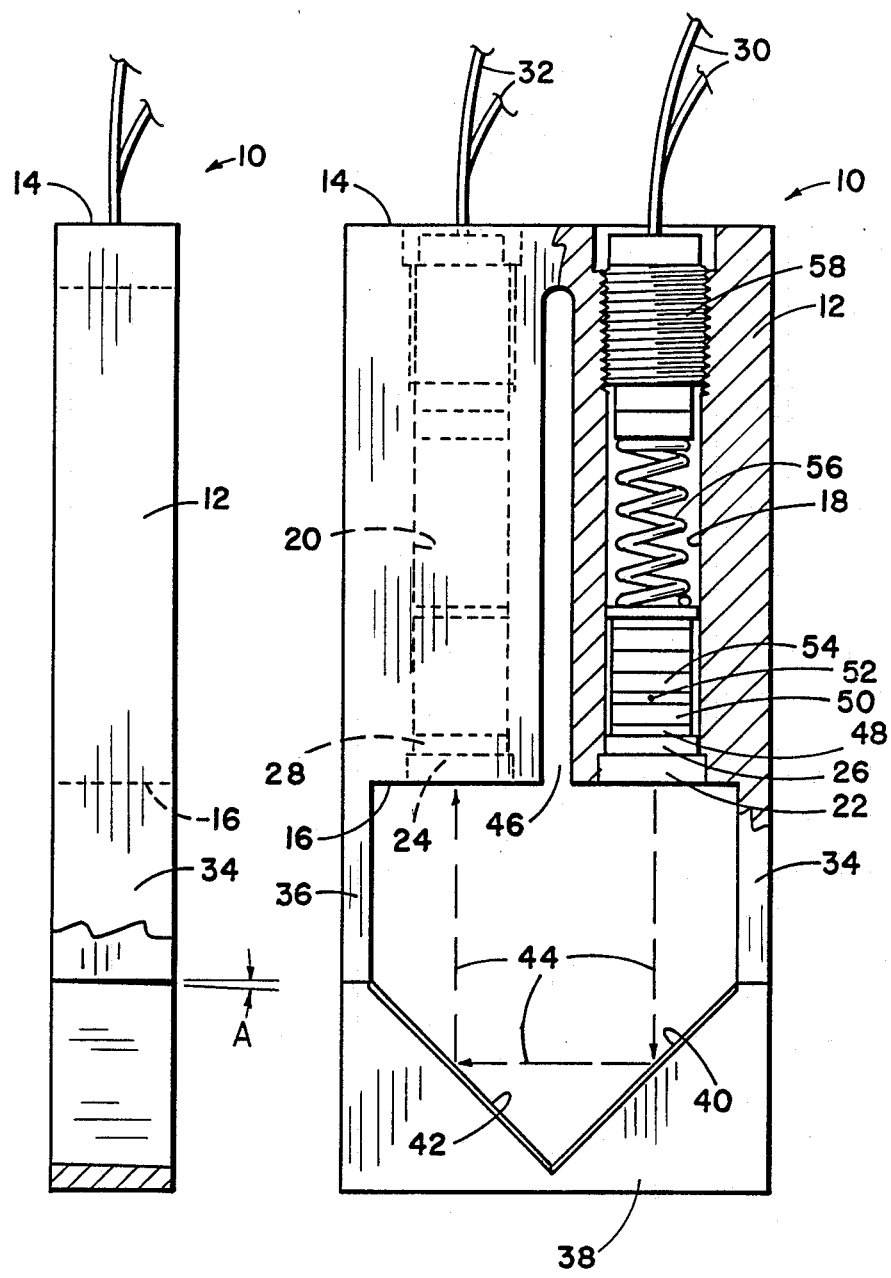
FIG. 1 is an elevational side view of an improved dual element transducer according to this invention for use in measuring the sound velocity characteristics of a fluid medium.
FIG. 2 is an elevational side view of the transducer of FIG. 1 with the lower target portion shown partially cut away.

Referring to the drawings and first to FIGS. 1 and 2, a preferred embodiment of the invention is illustrated. The dual element transducer is indicated generally by the numeral 10. The transducer 10 is formed of a body 12 which may be of metal, as illustrated, or of plastic materials. The body 12 has an access end 14 and an active end 16. Extending between the access end 14 and active end 16 is a first cylindrical opening 18 and spaced from and parallel to it, and preferably in a common plane therewith, is a second cylindrical opening 20.

A first acoustic window 22 closes first cylindrical opening 18 at the active end 16. In like manner, a second acoustic window element 24 closes cylindrical opening 20. A first transducer crystal element 26 is positioned in the first cylindrical opening 18 and in intimate contact with the first acoustic window 22. In like manner, a second crystal element 28 is positioned in cylindrical openings 20 and in contact with a second acoustic window 24.

First crystal element 26 will be deemed the transmitting crystal element and the second crystal element 28 as the receiving element; that is, when shocked by an electric voltage pulse, the first crystal element 26 deforms in a predetermined frequency, transmitting a sound pulse through acoustic window 22. This sound pulse is received in a manner to be described subsequently through the second acoustic window 24 to deform the receiving crystal element 28. The deformation thereof generates an electrical signal. The time spacing between the electric pulse which actuates the first crystal element 26 and the electric pulse generated by second crystal element 28 indicates the time of travel required for the sound pulse leaving the first crystal element 26 to the time of reception by second crystal element 28. This travel time provides information which can be employed to determine the sound velocity characteristics of the fluid medium in the sound transmission path. Thus, electrical pulsing signals are applied to conductors 30 to stimulate the first crystal element 26, and voltage signals representing the reception of the sound wave by the second crystal element 28 are provided on conductors 32.

Extending from the active end 16 of body 12 are integral leg portions 34 and 36. Affixed to the leg portions is a reflector element 38. It can be seen that the leg portion 34 can either be an integral part of body 12 or the sound reflector 38 or, if important and machining expenses are of no consequence, the sound reflector 38, leg portions 34 and 36 and body 12 can be integrally formed as a unity element.

Sound reflector 38 provides a first reflector surface 40 and a second reflector surface 42. The surfaces 40 and 42 are preferably planar and are inclined towards each other. The first reflector surface 40 is positioned in the path coincident with the cylindrical axis of the first cylindrical opening 18 and in like manner, the second reflector surface 42 is positioned to be coincident with the cylindrical axis of the second cylindrical opening 20. When a sound pulse is generated by first crystal element 26, it passes through the acoustic window 20 and follows the sound path as indicated by the dashed arrows 44. This sound path travels from the first acoustic window 22, to first reflector surface 40, from the first reflector surface 40 to the second reflector surface 42, and from the second reflector surface 42 through the second acoustic window 24 to the second crystal element 28. The length of this sound path 24 is precisely determinable, therefore, when the time lapse between the transmission of a sound pulse by crystal 26 and the reception thereof of crystal 28, the sound velocity characteristic of the medium which fills the sound path 44 is determined. For the operation of the transducer 10, at least all of that area of the transducer between the active end 16 and the reflective surfaces 40 and 42 must be filled with the fluid medium for which a sound velocity characteristic is to be determined.

As previously indicated, the use of dual element transducers has experienced some difficulty in the past, since the sound path 44 can function in two directions, that is, when a sound pulse strikes the second acoustic window 24 a portion of the sound is reflected back and this portion will return to impinge upon first acoustic window 22. At this point it is again reflected so that the path is retraced and subsequently a second sound pulse is received at second acoustic window 24 and passed to the second crystal element 28. To diminish the opportunity for this reflective signal or echo signal causing a spurious measurement, an important feature of this invention is the provision wherein the first reflector surface 40 and the second reflector surface 42 are each tilted somewhat relative to the plane of the sound transmission path 44. Thus, the plane of first reflector surface 40 which intersects the plane of the sound path 44, which plane is the same plane as that which is coincident with the cylindrical axes of first cylindrical opening 18 and second cylindrical opening 20 will not be perpendicular, but will be off set. That is, the plane of first reflector surface 40 is tilted such as 1°, the angle of tilt being illustrated by the angle "A" in FIG. 2. When the acoustic path 44 is in the order of about three inches, a tilt angle "A" of 1° serves to significantly diminish the reflection problem. If the acoustic path is shorter, the angle "A" may be increased, and if longer, the angle "A" may be decreased. While only one of the reflector surfaces 40 or 42 may be provided with an angle of deflection which reduces the portion of the signal transmitted on path 44, the preferred arranged is that both the surfaces 40 and 42 be set at an angle "A."

As previously indicated, one of the serious problems in the use of dual transducer elements wherein the transmitter element and the receiving element are closely juxtaposed in the same transducer body is that the sound generated by the transmitting transducer is directly coupled by the body itself to the receiving transducer which direct coupling sometimes masks or drastically interferes with the reflected sonic signal.

The transducer of FIGS. 1 and 2 includes an elongated slot 46 which extends from the transducer body active end 16 to adjacent the access end 14. Slot 46 extends the full width of the transducer body and provides sound isolation between the first or transmitting crystal element 26 and the second or receiving crystal element 28. It can be seen in FIG. 1 that for the sound to travel within the body itself, a long path is established by the provision of slot 46. This long path results in the intensity transmitted through the body being substantially diminished to thereby dramatically minimize the effect of the close proximity of the transmitting and receiving crystals.

In order to effectively dampen the sound generated by the transmitting crystal element 26 but at the same time to insure intimate acoustical contact between the crystal element and window 22, provision is made for applying force against the rearward surface of the crystal element. Reference is made to U.S. Pat. No. 4,763,513 which is incorporated herein by reference for detailed teaching of a preferred damping means. Generally speaking, this damping means includes a damping element 48 which contacts the rearward surface of the crystal element 26. A thrust disc 50 is in contact with the damping means 48. A thrust transmitting sphere 52 is positioned between the first thrust disc 50 and the second thrust disc 54 to insure that the load applied against the first thrust disc 50 is equally distributed against the rearward face of first crystal element 26. A spring 56, under compression, applies a uniform thrust to insure intimate contact between the crystal element 26 and acoustic window 22. The screw member 58 is used to adjust the compression on spring 56. All of the elements 48 through 58 are well described in U.S. Pat. No. 4,763,513. While the similar elements are not illustrated within the second cylindrical opening 20, such may be employed to insure intimate contact between the second crystal element 28 and the second acoustic window 24.

Figure 3:
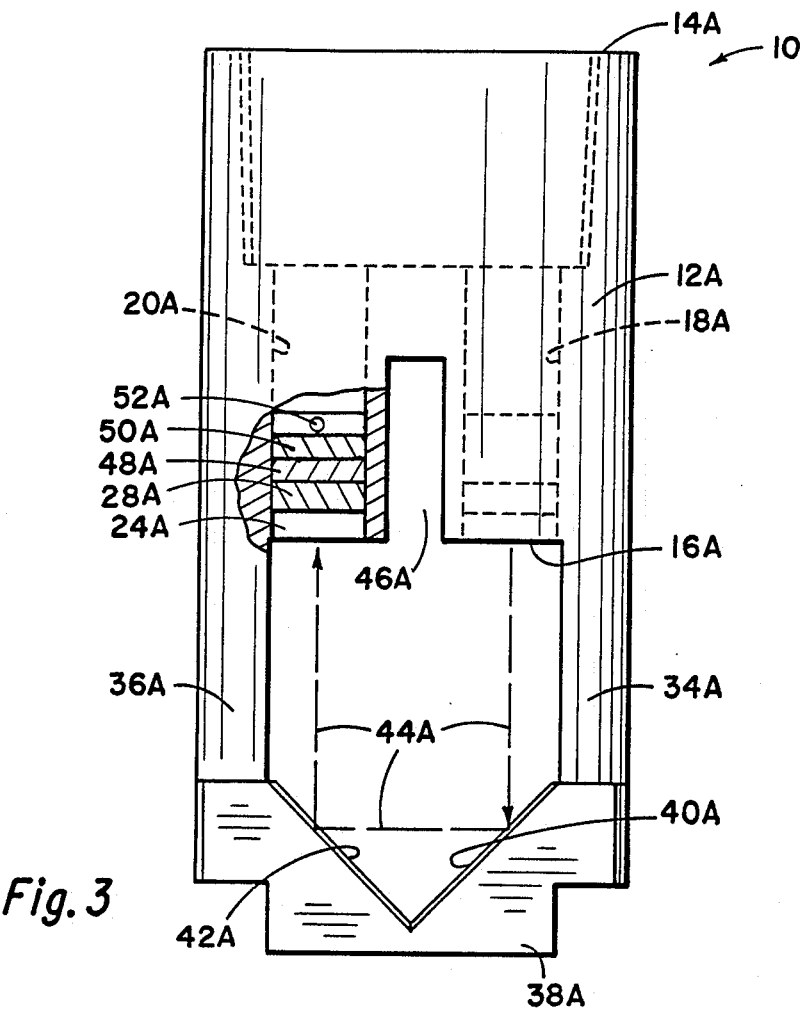
FIG. 3 is an elevational view of an alternate embodiment of the invention wherein the body is cylindrical, the view being partially cut away to show typical features of one of the transducers.
Figure 4:
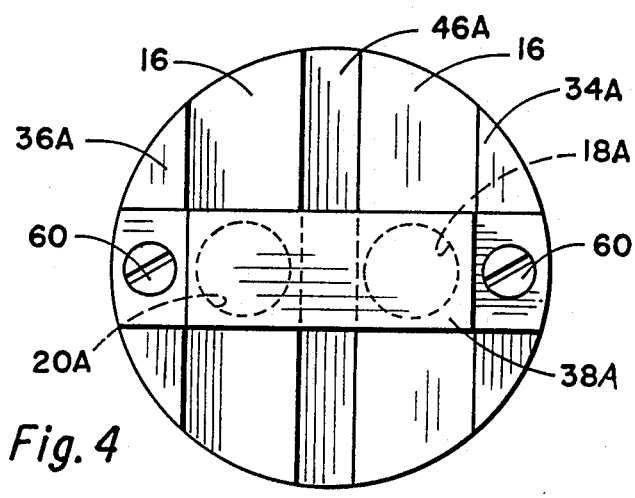
FIG. 4 is an end view of the lower end of the transducer of FIG. 3.

FIGS. 3 and 4 show an alternative embodiment of the invention which is different primarily in the shape of the transducer body. The reference numerals used to identify elements in FIGS. 3 and 4 superceded by an "A" corresond to the same elements having the same numbers in FIGS. 1 and 2. While in FIGS. 1 and 2 the transducer body 12 is rectangular in cross-sectional configuration, in FIGS. 3 and 4 the transducer body 12A is cylindrical which, in some applications, is advantageous in that it is easier to mount a cylindrical transducer body for fluidtight applications. While not shown, the cylindrical body 12A of FIGS. 3 and 4 may be externally threaded in part as a means of mounting it to other equipment.

The cylindrical transducer body 12A includes a longitudinal slot 46A, as previously mentioned. FIG. 3 shows a slot slightly wider and shorter, indicating that the width and length of the slot may be varied according to the specific design parameter of the transducer. FIG. 3 shows the elements for damping the transducer in the second cylindrical opening 20A of the type previously described with reference to FIG. 1.

Whereas, in FIGS. 1 and 2, the sound reflector 38 is of cross-sectional dimensions generally the same as the body 12. FIGS. 3 and 4 show the arrangement wherein the sound reflector element 38A is different in cross-section than body 12A. As illustrated in FIG. 4, the sound reflector 38A is of cross-sectional dimensions similar to that in FIGS. 1 and 2. The use of a sound reflector having the same cross-sectional dimensions as the body 12A is not necessary, however, it should be understood that the sound reflector can, if desired, have a circular cross-sectional configuration as does body 12A. The sound reflector 38A may be integrally formed with the body 12A or may be formed separately and attached to it, such as by welding, or by means of screws 60. The reflective surfaces 40A and 42A of the sound reflector 38A may also include, as illustrated, the arrangement wherein the planes are askewed compared to planes perpendicular to the plane of the sound path 44A to thereby decrease the effect of echo sound pulses being reflected sequentially from the acoustic windows.

FIGS. 3 and 4 illustrate the fact that the physical appearance of transducers which incorporate the principles of this invention may vary considerably.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A transducer for use in measuring the sound velocity characteristics of a fluid medium comprising:
    an elongated transducer body having an access end and an opposed active end, the body having elongated spaced apart first and second cylindrical openings therein extending from the access end and to the active end, the openings being generally parallel to each other and in a common plane;
    a first and a second acoustic window member sealably closing said first and second cylindrical openings in said body at said active end;
    a first and second transducer crystal element within respectively said first and second openings and in sonic contact with respectively said acoustic window members;
    a sound reflector affixed to said transducer body at said active end providing a first target surface in line with the cylindrical axis of said first opening and providing a second target surface in line with the cylindrical axis of said second opening, the target surfaces being spaced from said body active end and each being in a plane inclined toward the other, defining a sonic path from said first acoustic window member to said first target surface, from said first target surface to said second target surface, and from said second target surface to said second acoustic window member, and providing means for fluid medium to freely pass through said sonic path, the sonic path being in said common plane of said transducer body cylindrical openings;
    means of providig separate electrical paths for the stimulation of one of said crystal elements and for carrying signals generated by the other said crystal element; and the transducer body having an elongated slot therein between said cylindrical openings, the slot communicating with said body active end, the slot providing means of improving acoustic isolation of the portions of said body having said crystal elements therein.

2. A transducer according to claim 1 wherein at least one of said first and second target surfaces is in a plane tilted relative to said common plane of said cylindrical openings.

3. A transducer according to claim 1 wherein both of said first and second target surfaces are in a plane titled relative to said common plane of said cylindrical openings.

4. A transducer according to claim 1 wherein said slot extends the full width of said body.

5. A transducer according to claim 1 wherein said body is rectangular in cross-section in a plane perpendicular the length thereof between said access end and said active ends and wherein said sound reflector is of substantially corresponding cross-section shape.

6. A transducer according to claim 1 wherein said body is of circular cross-section configuration in a plane perpendicular the length thereof between said access end and said active end.

* * * * *